United States Patent [19]

Takahashi et al.

[11] Patent Number: 4,904,802

[45] Date of Patent: Feb. 27, 1990

[54] IMIDES

[75] Inventors: Satoji Takahashi; Tadashi Takemoto, both of Yakkaichi, Japan

[73] Assignee: Ajinomoto Co., Inc., Tokyo, Japan

[21] Appl. No.: 202,565

[22] Filed: Jun. 6, 1988

[30] Foreign Application Priority Data

Jun. 30, 1987 [JP] Japan .................................. 62-162940
Sep. 14, 1987 [JP] Japan .................................. 62-230697
Nov. 2, 1987 [JP] Japan .................................. 62-278098
Dec. 28, 1987 [JP] Japan .................................. 62-331889

[51] Int. Cl.$^4$ .......................................... C07D 207/416
[52] U.S. Cl. .................................................... 548/546
[58] Field of Search ........................................ 548/546

[56] References Cited

U.S. PATENT DOCUMENTS 3,211,747 10/1965 Johnson ............................... 548/546
3,433,801 3/1969 Dawson ............................... 548/546
4,757,146 7/1988 Maulding ............................ 548/546

Primary Examiner—David B. Springer
Attorney, Agent, or Firm—Oblon, Spivak, McClelland, Maier & Neustadt

[57] ABSTRACT

An imide of the formula:

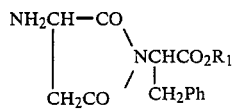

where $R_1$ is hydrogen or $C_{1-4}$ alkyl.

2 Claims, 1 Drawing Sheet

IMIDES

BACKGROUND OF THE INVENTION

1. Field of the Invention

The present invention relates to imide compounds, to a process for the production of the imide compounds from β-aspartylphenylalanine derivatives (β-AP derivatives), and to a process for the production of α-aspartylphenylalanine derivatives (α-AP derivatives) from the β-AP derivatives.

2. Description of the Background

Many processes are known for producing α-L-aspartyl-L-phenylalanine methyl ester (α-APM) which is useful as a sweetening agent. Many of the conventional processes comprise protecting the amino group of L-aspartic acid (L-Asp) by some means, for example, with a carbobenzoxy group, a formyl group, a hydrogen halide, or the like, and then dehydrating and condensing the protected aspartic acid with L-phenylalanine methyl ester to obtain an N-protected-L-aspartyl-L-phenylalanine methyl ester. Removal of the protective group then yields α-APM. However, in all of these processes, the formation of β-L-aspartyl-L-phenylalanine methyl ester (β-APM) as a by-product is inevitable.

Another method which is known involves the conversion of a β-aspartylphenylalanine derivative (formula (2)) into an α-aspartylphenylalanine derivative (formula (3)) and an α-aspartylphenylalanine anhydride derivative (DKP derivative) as shown in the following equation. This process is described in Japanese Patent Application Laid-open No. 277696/1986.

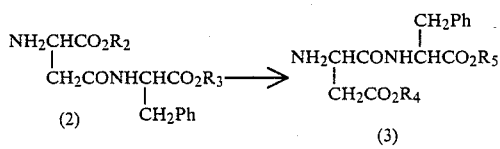

Although the α-AP derivative may be converted into the desired α-APM easily and in high yield, when the DKP derivative is employed as a reactant, it gives only a low yield of α-APM and large amounts of by-products are formed in the reaction. Further, the by-products which form are changed into substances which can never be converted into α-APM. Therefore, in order to maximize conversion to α-APM, the conversion of material into the DKP derivative is to be avoided.

SUMMARY OF THE INVENTION

Accordingly, one object of the present invention is to provide a method of synthesizing α-aspartylphenylalanine from β-APM or β-AP while avoiding the formation of α-aspartylphenylalanine anhydride.

Briefly, this object and other objects of the present invention as hereinafter will become more readily apparent can be attained in a method for synthesizing α-aspartylphenylalanine by converting a β-aspartylphenylalanine derivative of the formula:

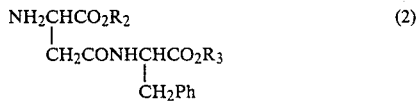

where $R_2$ and $R_3$ are each hydrogen or $C_{1-4}$ alkyl in a non-alcoholic solvent into an imide intermediate of the formula:

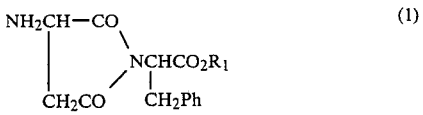

where $R_1$ is hydrogen or $C_{1-4}$ alkyl; and thereafter converting said imide into an α-aspartylphenylalanine derivative of the following formula in the presence of a base

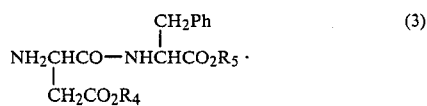

wherein $R_4$ and $R_5$ are each hydrogen or $C_{1-4}$ alkyl.

Another aspect of the invention is the provision of a cyclic imide of formula (1) prepared from β-aspartylphenylalanine as well as a method of synthesizing the imide compound.

BRIEF DESCRIPTION OF THE DRAWING

A more complete appreciation of the invention and many of the attendant advantages thereof will be readily obtained as the same becomes better understood by reference to the following detailed description when considered in connection with the accompanying drawing, wherein:

the FIGURE is an NMR spectrum (60 MHz) of the imidomethyl ester intermediate of the present invention.

DETAILED DESCRIPTION OF THE PREFERRED EMBODIMENTS

Figure 1:
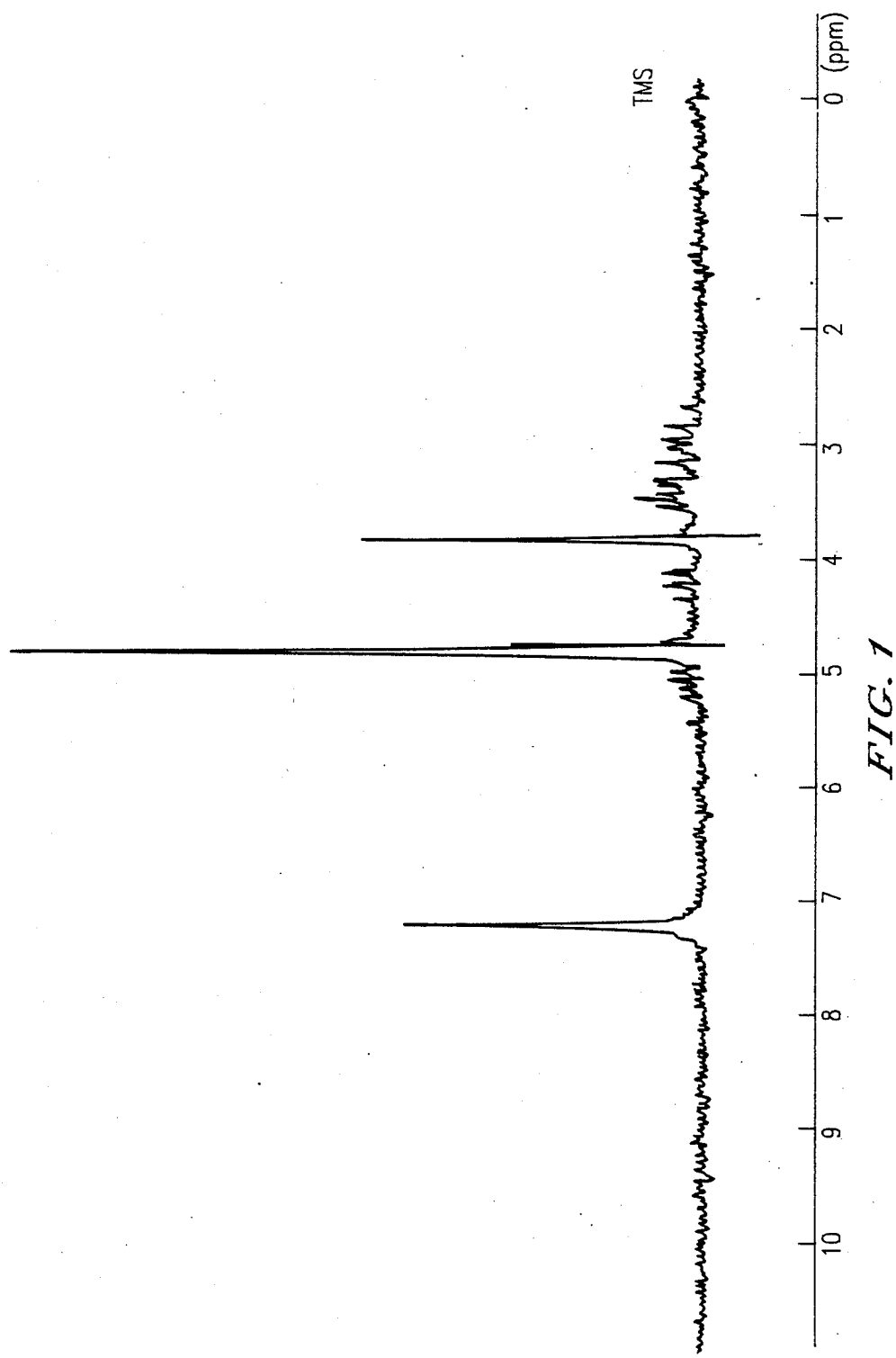

In the process of the invention a β-AP derivative is converted into an α-AP derivative by a first reaction in which a β-AP derivative is placed in a non-alcoholic solvent in the presence or absence of an acid catalyst with stirring or without stirring. A reaction occurs in which the imide compound of formula (1) is formed as an intermediate. A second reaction is then initiated by adding a basic catalyst to the reaction medium during the first reaction or after the first reaction has been completed.

The α-AP derivative which is formed by the process of the present invention may be easily converted into α-APM by any known technique. For example, α-APM may be produced in the form of the hydrochloride (α-APM .HCl) by placing the ester in an aqueous solution containing HCl and methanol (Japanese Patent Application Laid-open No. 129258/1984).

The starting material of the present process is the β-AP derivative of formula (2). Preferred specific embodiments of the β-AP derivative include β-aspartylphenylalanine dimethyl ester (β-aspartylphenylalanine methyl ester in which the α-carboxyl group of the aspartic acid residue has been methyl esterified) (β-APM$_2$) and β-aspartylphenylalanine α-methyl ester (β-aspartylphenylalanine in which the α-carboxyl group of the aspartic acid residue has been methyl esterified) (β-A(M)P). The starting material can tolerate the presence of α-AP derivatives.

The β-AP derivative of formula (2) may be produced by any known method. For example, the β-AP derivative of formula (2), where $R_2$ is hydrogen, may be prepared by protecting the α-carboxyl group of the aspartic acid by, e.g., benzyl esterification, and then protecting the N-terminal of the amino acid with a conventionally used protecting group. The resulting compound is then reacted with a phenylalanine alkyl ester in the presence of a condensing agent such as dicyclohexylcarbodiimide, thereby yielding an N-protected-aspartylphenylalanine alkyl ester and thereafter removing the N-protecting group and the benzyl ester group in a conventional manner.

In the case of the β-AP derivative where $R_3$ is hydrogen, the compound may be prepared by alkylating the α-carboxyl group of aspartic acid, protecting the N-terminal of the acid with a conventinal protecting group, reacting the protected compound with phenylalanine whose α-carboxyl has been benzyl esterified in the presence of a condensing agent as in the above-described technique, and thereafter removing the N-protecting group and the benzyl ester group in a conventional manner.

Still further, in the case where $R_2$ and $R_3$ of the β-AP derivative are both alkyl groups, the compound may be prepared by condensing an N-protected-α-carboxyl-alkylated-aspartic acid with an α-carboxyl-alkylated-phenylalanine by the process described above, and thereafter removing the N-protecting group in a conventional manner. Furthermore, where $R_2$ and $R_3$ of the β-AP derivative are both hydrogen, the compound may be prepared by the alkali saponification of any of the above three alkyl esters.

The β-AP derivative of formula (2) may be employed as such, as an N-protected -β-aspartylphenylalanine alkyl ester (or dialkyl ester) in the reaction without removing the N-protecting group.

Further, the β-AP derivative of formula (2) may be in the form of a salt such as the hydrochloride, a sulfate or the like.

The synthesis conditions for the conversion of the compound of formula (2) to the compound of formula (1) and compound of the formula (3) are described below.

The solvent which is employed in the reaction medium is not particularly limited and may be selected from a wide group of solvents as long as alcoholic solvents are excluded from the first-stage reaction in which the β-AP derivative is converted to the imide of formula (1). Suitable solvents include aromatic hydrocarbons such as benzene, toluene, or the like; halogenated hydrocarbons such as dichloroethane, or the like; hydrocarbons such as pentane, hexane, or the like; ketones such as acetone, methyl ethyl ketone, diethyl ketone, or the like; fatty acid esters such as ethyl acetate, butyl acetate, or the like; fatty acids such as acetic acid, propionic acid, or the like; alcohols such as methanol, ethanol, isopropanol, butanol, or the like; and water. Of course, mixtures of various solvents may also be employed. Especially preferred for the first-stage reaction are aromatic hydrocarbon, halogenated hydrocarbon, ketone and fatty acid ester solvents. For the second-stage reaction, in addition to the above preferred solvents of the first stage, alcoholic solvents and mixed solvents of water and alcohol may be used. When water is added, it is used in an amount of 1–10 mole per mole of the compound of formula (1).

The amount of the solvent employed is not particularly limited, but, in general, 0.5–200 times by weight of the solvent is employed based on the amount of β-AP derivative employed.

The catalyst which is used in the above-described first-stage reaction may be omitted, but if an acid is added, the rate of the intermediate derivative formation is increased and thus the use of an acid catalyst is preferred. While the acid catalyst added is not particularly limited, preferred acids include mineral acids such as sulfuric acid, hydrochloric acid, phosphoric acid, nitric acid, and the like; fatty acids such as formic acid, acetic acid, propionic acid, and the like; and Lewis acids such as aluminum chloride, and the like. The amount of the acid added is not particularly critical, but it is advantageous from an economical point of view to use 0.001–20 mole per mole of the β-AP derivative, and in general, 0.01–2 mole per mole is used.

A basic catalyst is employed in the second-stage reaction. Suitable basic catalysts include the likes of inorganic bases such as sodium hydroxide, potassium hydroxide, calcium hydroxide, sodium carbonate, sodium bicarbonate and the like and organic bases such as triethylamine, and the like. The amount of the base employed preferably ranges from 0.01–5 mole per mole of the imide derivative used in this reaction from an economic point of view. Further, the addition of an inorganic or organic compound of a metal such as zinc, copper, nickel or the like can be made. Suitable compounds include $ZnCl_2$, $ZnSO_4$, $CuCl_2$, $NiCl_2$, and the like. The compound is used in an amount of 0.01–2 mole, preferably 0.1–1.0 mole per mole of the imide of formula (1). The compound within these amounts increase the yield of product.

The reaction temperature for the first stage is normally in the range of $-10°$ to $200°$ C. However, at low temperatures, the reaction rate is diminished. While it is not necessary to employ excessively high temperatures, the temperature employed is usually in the range of $0°-150°$ C.

The reaction temperature for the second stage is normally in the range of $-30°$ to $100°$ C. If the temperature is too high, side reactions such as polymerization will occur. Accordingly, the temperature is usually in the range of $-20°$ to $80°$ C.

The reaction time for the first stage varies depending on the amount of the catalyst used and the reaction temperature. Normally, it is within the range of from 10 minutes to 30 hours. The reaction time for the second stage varies depending on the amount of the catalyst used and the reaction temperature, and is normally within the range of from 1 minutes to 10 hours.

The present process has the advantage that the α-AP derivative may be synthesized from the β-AP derivative without the formation of the DKP derivative or with the formation of the DKP derivative in only very small amounts. Further, the by-products in the liquid reaction mixture are mainly the β-AP derivative of formula (2). Thus, the reaction medium can be recycled as a starting material to conduct further processing.

The method for converting the reaction mixture of the present invention containing the α-AP derivative into α-APM and separating the α-APM may be effected by any known method. For example, although it is possible to separate the α-AP derivative from the reaction medium, it is generally advantageous to remove the solvent by distillation, and then convert the α-AP derivative into α-APM.HCl by the method described above (Japanese Patent Application Laid-open No. 129258/1984) and then obtain α-APM.

Having generally described this invention, a further understanding can be obtained by reference to certain specific examples which are provided herein for purposes of illustration only and are not intended to be limiting unless otherwise specified.

EXAMPLES

Example 1

To 1.2 l of a toluene solution containing 61.6 g of $\beta$-L-aspartyl-L-phenylalanine dimethyl ester ($\beta$-L-aspartyl-L-phenylalanine methyl ester in which the $\alpha$-carboxyl group of the L-aspartic acid has been methyl esterified) ($\beta$-APM$_2$(L/L)) was added 1.2 ml of 98 wt % sulfuric acid. The reaction medium was heated with stirring at 103° C. for 11 hours. The medium was then cooled to 30° C., and toluene was added until the reaction mixture reached 1.5 l in total volume.

A 1.0 ml sample was taken from this reaction mixture and quantitatively analyzed for the intermediate derivative; N-(1-carbomethoxy-2-phenylethyl)-2-aminosuccinimide (imidomethyl ester) by high performance liquid chromatography (HPLC). The yield of the imidomethyl ester was 98.7%, and the yield of the $\beta$-APM$_2$ (L/L) starting material was 1.0%.

The physical property values of the formed imidomethyl ester are as follows:

Elemental Analysis for $C_{14}H_{16}N_2O_4$: Calculated: C: 60.86, H: 5.84, N: 10.14 Found: C: 60.78, H: 5.80, N: 10.21.

The NMR spectrum of the imidomethyl ester is shown in FIG. 1.

Further, 900 ml of the above-described reaction mixture was distilled to remove the toluene under reduced pressure, then 600 ml of methanol was added thereto and cooled to 20° C. Thereafter, 120.0 ml of a methanol solution of 1 mole/l of potassium hydroxide was added thereto and reacted for an hour. A 1.0 ml sample of this reaction mixture was taken and quantitatively analyzed for $\alpha$-aspartylphenylalanine dimethyl ester ($\alpha$-aspartylphenylalanine methyl ester in which the $\beta$-carboxyl group of the aspartic acid has been methyl esterified) $\alpha$-APM$_2$). The yield of $\alpha$-APM$_2$ obtained, based on the imidomethyl ester, was 55.4%.

The methyl ester of $\alpha$-aspartylphenylalanine anhydride was not detected, and $\beta$-APM$_2$ was detected in an amount of 35.1%.

EXAMPLE 2

150 ml of the reaction mixture of the imidomethyl ester obtained in Example 1 (the reaction mixture diluted with toluene to 1.5 l in total volume) was distilled under reduced pressure to remove the toluene. After adding 100 ml of methanol, it was cooled to 0° C., and 0.8 g of sodium hydroxide was added, and the medium was stirred for 1.5 hours.

When quantitatively analyzed by HPLC, $\alpha$-APM$_2$ had been produced in an amount of 52.8% based on the imidomethyl ester.

EXAMPLE 3

75 ml of the reaction mixture of the imidomethyl ester obtained in Example 1 (the reaction mixture diluted with toluene to 1.5 l in total volume) was distilled under reduced pressure to remove the toluene. After adding 100 ml of acetone, it was cooled to 5° C., then 15 ml of a 1M/l aqueous potassium hydroxide solution was added and reacted for 1.5 hours.

When quantitatively analyzed by HPLC, $\alpha$-aspartylphenylalanine ($\alpha$-AP) had been produced in a yield of 32.5% based on the imidomethyl ester.

EXAMPLE 4

The reaction was accomplished in a manner similar to that in Example 3 except that after removing toluene by distillation, water was added instead of acetone.

When $\alpha$-AP was quantitatively analyzed by HPLC, it had been produced in a yield 28.8% based on the imidomethyl ester.

EXAMPLE 5

75 ml of the reaction mixture of the imidomethyl ester obtained in Example 1 (the reaction mixture diluted with toluene to 1.5 l in total volume) was maintained at 40° C., 10.0 ml of a methanol solution of 1M/l potassium hydroxide was added, and the resulting solution was stirred for 30 minutes.

After the reaction, the toluene and the methanol was removed by distillation under reduced pressure, 20.0 ml of a 1M/l aqueous sodium hydroxide solution was added, and reacted at 40° C. for 3 hours to effect saponification, followed by quantitative analysis for $\alpha$-AP by HPLC. It was found that $\alpha$-AP had been produced in an amount of 29.0% based on the imidomethyl ester.

EXAMPLE 6

To 100 ml of methanol were added 28.0 g of $\beta$-L-aspartylphenylalanine and 6.0 ml of 98 wt % sulfuric acid, followed by heating at reflux for 4.5 hours. Then, the methanol was removed by distillation under reduced pressure and 200 ml of toluene was added. The resulting mixture was reacted at 103° C. with stirring for 15 hours.

This reaction mixture was quantitatively analyzed for the imidomethyl ester by HPLC and it was found that the imidomethyl ester had been produced in a yield of 99.5%.

EXAMPLE 7

28.0 g of $\beta$-A(M)P was suspended in 500 ml of toluene. A 0.6 ml amount of 98 wt % sulfuric acid was added and the mixture was stirred at 103° C. for 20 hours. After cooling to 20° C., 250 ml of a 1M/l aqueous sodium hydroxide solution was added and stirred for an hour. $\alpha$-AP was quantitatively analyzed by HPLC and it was found that $\alpha$-AP had been produced in an amount of 36.5% based on $\beta$-A(M)P.

EXAMPLE 8

3.57 of $\beta$-L-aspartyl-L-phenylalanine dimethyl ester hydrochloride ($\beta$-APM$_2$(L/L)) was suspended in 100 ml of toluene, 0.21 g of triethylamine was added, and stirred at 100° C. for 30 hours. Then, 20 ml of a methanol solution of 1M/l potassium hydroxide was added, and reacted at 20° C. for 30 minutes. Thereafter, 20 ml of a 1M/l aqueous potassium hydroxide solution was added, and the resulting mixture was stirred for 3 hours. Quantitative analysis by HPLC showed that $\alpha$-AP had been produced in an amount of 48.3%.

EXAMPLE 9

To 32.2 g of N-formyl-$\beta$-L-phenylalanine methyl ester were added 100 ml of methanol and 6.1 ml of 98 wt % sulfuric acid followed by heating at reflux for 6 hours. Thereafter, the methanol was removed by distillation under reduced pressure, 200 ml of toluene was added, and reacted at 103° C. with stirring for 16 hours. This reaction mixture was quantitatively analyzed for the imidomethyl ester by HPLC, and it was found that it had been produced in an amount of 90.5%.

Further, in this example, when 30.8 g of N-formyl-β-L-aspartyl-L-phenylalanine was employed as the starting material, the imidomethyl ester was produced in a yield of 91.3%.

EXAMPLE 10

To 0.8 l of a toluene solution containing 30.8 g of β-APM$_2$ was added 0.55 ml of 98 wt % sulfuric acid. The resulting mixture was heated with stirring, and reacted at 100° C. for 6 hours. The imidomethyl ester was produced in a yield of 98.0%. Thereafter, the toluene was removed by distillation under reduced pressure. 0.4 ml of methanol was added to the resulting material, and the mixture was divided equally into 5 portions. To the respective portions, the ingredients shown below were added followed by the addition to each portion of 21 ml of a methanol solution of 2M/l potassium hydroxide at 20° C. with stirring. Ten minutes later, α-APM$_2$ was quantitatively analyzed for by HPLC. The results obtained for each portion are shown in the table.

| Experiment No. | Additive | Based on the imidomethyl ester (mole times) | Yield of -APM$_2$ Based on the imidomethyl ester (%) |
|---|---|---|---|
| 1 | ZnSO$_4$.7H$_2$O | 0.5 | 65.7 |
| 2 | ZnCl$_2$ | 0.5 | 65.7 |
|   | H$_2$O | 3.5 |  |
| 3 | CuCl$_2$ | 0.5 | 58.2 |
|   | H$_2$O | 3.5 |  |
| 4 | ZnCl$_2$ | 0.5 | 57.3 |
|   | Ion exchange | 50 ml |  |

| Experiment No. | Additive | Based on the imidomethyl ester (mole times) | Yield of -APM$_2$ Based on the imidomethyl ester (%) |
|---|---|---|---|
|   | resin* |  |  |

*"Diaion CR10" produced by Mitsubishi Chemical Industries, CO., Ltd.

COMPARATIVE EXAMPLE

To the whole volume of the reaction mixture which had been treated with potassium hydroxide in Example 1 (excluding 1.0 ml taken as the sample) were added 50 ml of a 35% aqueous hydrochloric acid solution and 50 ml of water, followed by concentration of the reaction medium under reduced pressure to a liquid volume of about 100 ml. To this concentrated liquor was added 6.0 ml of methanol, maintained at 20° C. with stirring for 7 days, and then maintained at 5° C. for 2 days. The separated APM.HCl crystals were filtered, 300 ml of water was added, and the mixture was neutralized with a aqueous Na$_2$CO$_3$ solution to adjust the pH to 4.5. The mixture was heated to 60° C. to dissolve the APM and was left to stand at 5° C. for 24 hours. The separated crystals were filtered and dried by heating under reduced pressure, thereby yielding 12.1 g of α-APM crystals (34.3% based on β-APM$_2$).

Having generally described this invention, a further understanding can be obtained by reference to certain specific examples which are provided herein for purposes of illustration only and are not intended to be limiting unless otherwise specified.

What is new and desired to be secured by letters patent of the United States is:

1. An imide of the formula:

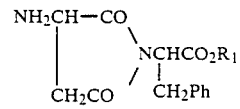

where R$_1$ is hydrogen or C$_{1-4}$ alkyl.

2. The imide according to claim 1, wherein R$_1$ is hydrogen or methyl.

* * * * *